United States Patent
Erb et al.

(10) Patent No.: US 6,436,119 B1
(45) Date of Patent: *Aug. 20, 2002

(54) ADJUSTABLE SURGICAL DILATOR

(75) Inventors: Steven J. Erb; Britt Norton, both of Eden Prairie, MN (US)

(73) Assignee: Raymedica, Inc., Bloomington, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/409,129

(22) Filed: Sep. 30, 1999

(51) Int. Cl.[7] .............................................. A61M 29/00
(52) U.S. Cl. ......................... 606/198; 606/61; 606/185
(58) Field of Search ........................ 606/61, 191, 198, 606/72, 232, 185; 411/15, 44, 57, 63, 45; 30/366, 368; 600/190, 196, 222, 224; 604/164.03, 164.06, 164.1, 264

(56) References Cited

U.S. PATENT DOCUMENTS

| | | | | |
|---|---|---|---|---|
| 84,815 A | * | 12/1868 | Garrin ......................... 606/198 |
| 765,879 A | * | 7/1904 | Campbell .................... 606/198 |
| 3,486,505 A | * | 12/1969 | Morrison ..................... 606/61 |
| 3,875,595 A | | 4/1975 | Froning |
| 4,349,921 A | | 9/1982 | Kuntz |
| 4,545,374 A | * | 10/1985 | Jacobson ..................... 606/61 |
| 4,772,287 A | | 9/1988 | Ray |
| 5,047,055 A | | 9/1991 | Bao |
| 5,171,280 A | | 12/1992 | Baumgartner |
| 5,192,326 A | | 3/1993 | Bao |
| 5,263,937 A | * | 11/1993 | Shipp .......................... 604/164 |
| 5,300,070 A | * | 4/1994 | Gentelia et al. ............ 604/164 |
| 5,443,514 A | | 8/1995 | Steffee |
| 5,674,295 A | | 10/1997 | Ray |
| 5,676,681 A | * | 10/1997 | Yoon ........................... 604/164 |
| 5,720,753 A | * | 2/1998 | Sander et al. ................. 606/72 |
| 5,766,252 A | | 6/1998 | Henry |
| 5,800,549 A | | 9/1998 | Bao |
| 5,824,002 A | * | 10/1998 | Gentelia et al. ............ 604/164 |
| 6,162,236 A | * | 12/2000 | Osada ........................ 604/264 |

FOREIGN PATENT DOCUMENTS

FR          2639823        6/1990

* cited by examiner

*Primary Examiner*—Michael J. Milano
*Assistant Examiner*—Julian W. Woo
(74) *Attorney, Agent, or Firm*—Dicke, Billig & Czaja, P.A.

(57) ABSTRACT

An adjustable surgical dilator for dilating an opening formed in a bodily tissue structure, such as an anulus of a spinal disc. The dilator includes an outer tube and an inner rod. The outer tube includes a proximal section, a distal section and a central lumen extending from the proximal section to the distal section. The distal section terminates in a distal end and includes first and second arms each defining an inner surface and an outer surface. The arms combine to define a head tapering to the distal end. The head is configured to contact bodily tissue and has a variable cross-sectional outer dimension as defined by the outer surfaces of the arms. The inner rod is co-axially disposed within the central lumen and includes a proximal portion and a distal portion. The distal portion extends from the proximal portion and forms a bearing surface for selectively engaging the inner surfaces of the first and second arms, respectively. With this engaging relationship, the inner rod, and in particular the bearing surface, controls the variable cross-sectional outer dimension of the head. With this configuration, the inner rod is axially movable relative to the outer tube for providing selective positioning of the bearing surface relative to the first and second arms, thereby dictating a desired outer dimension of the head.

33 Claims, 9 Drawing Sheets

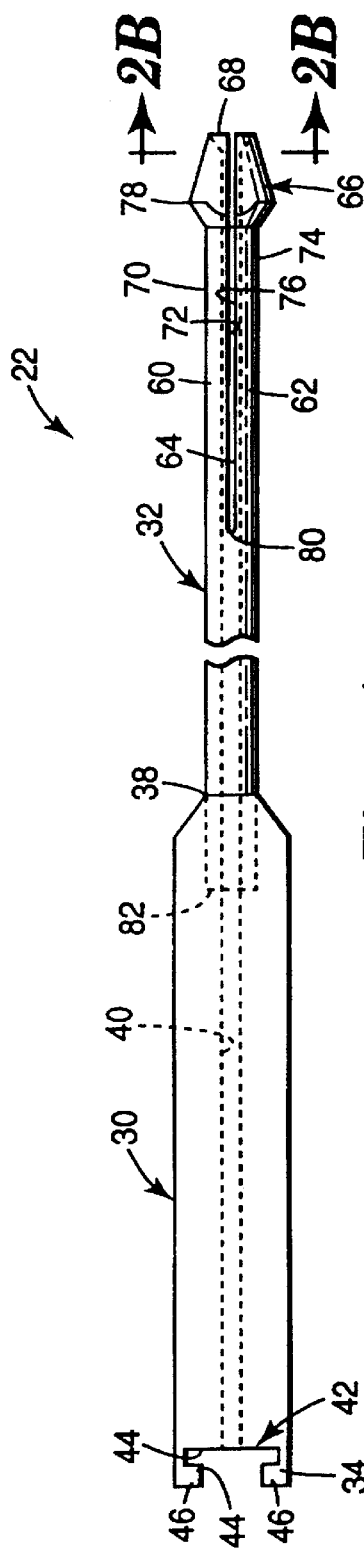
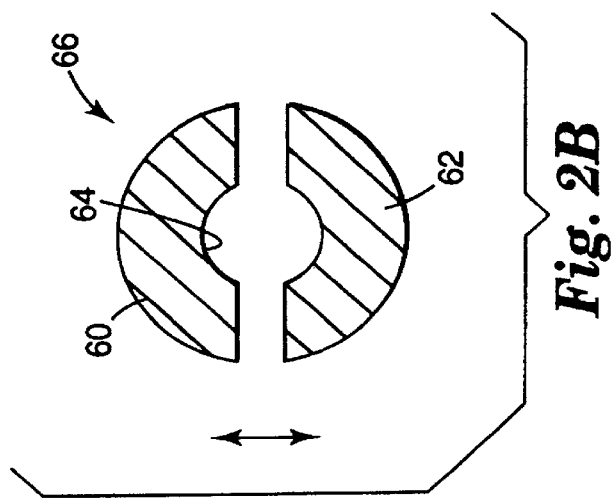
Fig. 2A
Fig. 2B

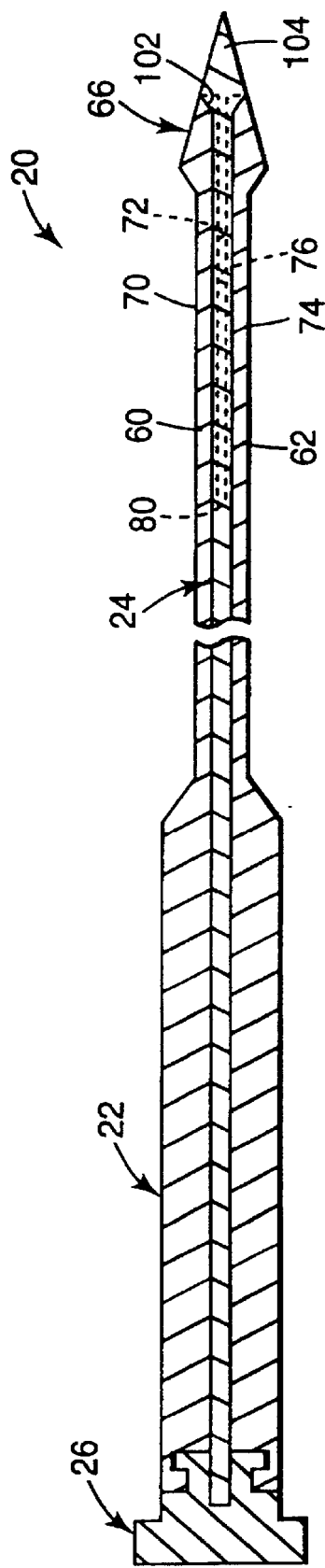
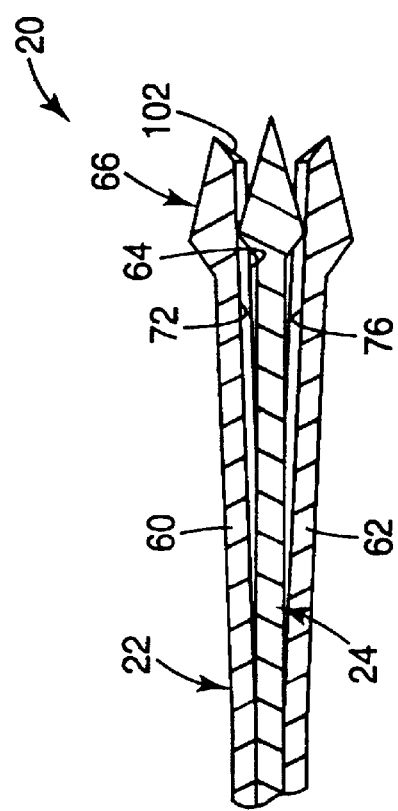
Fig. 6A
Fig. 6B

ADJUSTABLE SURGICAL DILATOR

BACKGROUND OF THE INVENTION

The present invention relates to a surgical device for dilating an opening formed in a bodily tissue structure. More particularly, it relates to a hand-held instrument configured to provide controlled dilation of an opening in a bodily tissue structure, such as an anulus of a spinal disc.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, and a neural (vertebral) arch that arises from a posterior surface of the vertebral body. Each narrow arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portions of adjacent vertebrae are separated and supported by an intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space and were large and rigid. Beyond the questionable efficacy of these devices is the inherent difficulties encountered during implantation. Due to their size and inflexibility, these first generation devices require an anterior implantation approach as the barriers presented by the lamina and, more importantly, the spinal cord and nerve rootlets during posterior implantation, could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced size prostheses are intended to serve as a replacement for the natural nucleus. In other words, the anulus and end plates remain intact, and the prosthesis is implanted within the nucleus cavity. Assuming that anulus integrity has not been overly compromised and that internal, lateral forces are minimized, the anulus will subsequently heal, resulting in a near-normal disc function. To this end, a number of different prosthetic nucleus designs have been developed. A common concern associated with these designs is minimizing stress placed on the anulus during implantation. In order to implant a prosthesis within the nucleus cavity, an appropriately sized passageway must be provided through the anulus. Obviously, reducing the overall size of the passageway minimizes resulting anulus trauma. With this in mind, two general design techniques have been identified for reducing the requisite anulus opening size. First, the prosthesis may be configured to increase from a relatively small size prior to implant, to a larger size following implant. With this approach, the reduced, pre-implant size of the prosthesis minimizes the requisite passageway size. Alternatively, the prosthesis may include several independent, relatively small portions, each of which are implanted through a correspondingly small passageway in the anulus. It should be understood that so long as it is minimized, "trauma" resulting from formation of the passageway is in no way permanent. Instead, the anulus tissue will regenerate, repairing the passageway.

While the particular prosthetic nucleus design selected has a distinct affect on resulting anulus damage, an equally important constraint is actual formation of the opening or passageway through the anulus. One technique entails complete removal of a plug of tissue from the anulus via an incision created by a scalpel, punch or similar tool. Entire removal of an anulus segment is highly traumatic, and limits the ability of the anulus to properly heal. Attempts to reattach the anulus plug have been unavailing in that properly orientating and securing of the anulus plug with a suture has proven difficult at best. Alternatively, a flap can be Imparted into the anulus tissue. This technique overcomes the reattachment problems associated with the anulus plug approach. Unfortunately, however, the thickness of the anulus requires formation of a relatively large flap, therefore increasing anulus trauma. Further, it may be difficult to retain the flap in a retracted position throughout the implantation procedure. A third, more viable procedure is to dilate a small opening or incision in the anulus to a size sufficient for prosthesis implantation. The overlapping, plied nature of the anulus tissue renders the anulus highly amenable to incision dilation.

An additional advantage presented by the above-referenced anulus incision dilation approach relates to the fact that in many circumstances, the anulus hag a preexisting opening through which the nucleus originally herniated. Thus, it may be unnecessary to initially impart an opening through the anulus. Alternatively, or in addition, a small incision can be made through the anulus. Regardless of how the opening is formed, subsequent dilation of the opening to a desired size typically requires the use of at least three different dilating tools. Each of the tools includes a tapered distal end of a fixed size configured to expand or dilate the opening upon insertion therein. Through successive use of increasingly larger tools, the anulus opening can be dilated to a desired size. While this technique has been successful, certain potential drawbacks have been identified. The requirement of three or more tools greatly increases the time required by a surgeon to complete the implantation procedure, and likewise increases the opportunity for error. Further, each insertion of an instrument into the anulus increases the likelihood of friction, trauma and impaction of tissue. As a result, the time required for the anulus to properly heal is likely increased, and may in fact be prevented from occurring.

Degenerated, painfully disabling intraspinal discs are a major economic and social problem for patients, their families, employers and the public at large. Any significant means to correct these conditions without further destruction or fusion of the disc may therefore serve an important role. To this end, prosthetic nucleus devices have shown great promise. As part of the implantation of such a device, however, current techniques and tools employed to create an anulus opening have not been perfected. Similar concerns exist for other bodily tissue structures, such as the knee, shoulder, etc. Therefore, a need exists for a singular device configured to adequately dilate an opening formed in a bodily tissue structure, such as an anulus.

SUMMARY OF THE INVENTION

One aspect of the present invention provides an adjustable surgical dilator for dilating an opening formed in a bodily tissue structure. The surgical device includes an outer tube and an inner rod. The outer tube includes a proximal section, a distal section and a central lumen. The distal section extends from the proximal section and terminates in a distal end. Further, the distal section includes first and second arms each defining an inner surface and an outer surface. The arms combine to form a head tapering in diameter to the distal end. The head is configured to contact bodily tissue and has a variable cross-sectional outer dimension as defined by the outer surfaces of the arms. In one preferred embodiment, the cross-sectional width of the head is variable. The inner rod is co-axially disposed within the central lumen of the outer tube. The inner rod includes a proximal portion and a distal portion. The distal portion extends from the proximal portion and forms a bearing surface for selectively engaging the inner surfaces of the first and second arms of the outer tube, respectively. With this selective engagement, the bearing surface controls the variable cross-sectional outer dimension of the head. Upon final assembly, the inner rod is axially movable relative to the outer tube to dictate a position of the bearing surface relative to the arms.

Prior to use, the inner rod is maneuvered relative to the outer tube such that the bearing surface does not engage the inner surfaces of the first and second arms. At this orientation, the head is relaxed or contracted, assuming a minimum cross-sectional outer dimension. The surgical device is then directed toward the bodily tissue structure in question, for example an anulus of a spinal disc. More particularly, the surgical device is positioned such that the head is placed within an opening formed in the bodily tissue structure such that the head contacts the bodily tissue. The inner rod is then co-axially maneuvered relative to the outer tube such that the bearing surface engages the first and second arms. Further axial movement of the inner rod, and thus of the bearing surface, causes the first and second arms, and in particular the head, to deflect radially. In other words, the variable cross-sectional outer dimension of the head increases or expands with further axial movement of the inner rod. Expansion of the head in turn dilates the tissue opening. Thus, by controlling the position of the inner rod relative to the outer tube, a surgeon dictates a final, dilated opening size. Further, the surgical device affords a surgeon the ability to control the rate at which dilation occurs.

Another aspect of the present invention relates to an adjustable surgical dilator for dilating an opening formed in a bodily tissue structure, such as an anulus of a spinal disc. The surgical device includes an outer tube and an inner rod. The outer tube includes a proximal section, a distal section and a central lumen. The distal section extends from the proximal section and terminates in a distal end. Further, the distal section includes a head and an axial slot. The head tapers in diameter distally to the distal end and is configured for contacting bodily tissue. The axial slot extends from the distal end to a point proximal the head. With this configuration, a variable outer cross-sectional dimension, preferably the width, of the head varies with radial expansion of the axial slot. Finally, the central lumen extends from the proximal section to the axial slot. The inner rod is co-axially disposed within the central lumen and includes a proximal portion and a distal portion. The distal portion extends from the proximal portion and forms a bearing surface for selectively engaging the distal section of the outer tube. the selective engagement controls radial expansion of the axial slot. With this configuration, the inner rod is axially movable relative to the outer tube for providing selective positioning of the bearing surface relative to the distal section of the outer tube.

During use, the inner rod is positioned so as to minimize radial expansion of the slot. With this orientation, the variable outer cross-sectional dimension of the head is as small as possible. The surgical device is then directed toward a bodily tissue structure such that the head is inserted into the opening in the tissue structure. The inner rod is axially maneuvered such that the bearing surface engages the distal section of the outer tube. Engagement of the bearing surface with the distal section causes radial expansion of the axial slot and thus an increase in the variable outer cross-sectional dimension of the head. Because the head is in contact with the tissue structure, this increase in cross-sectional diameter causes the opening to dilate. Further axial movement of the inner rod allows a surgeon to dilate the opening to a desired size.

Yet another aspect of the present invention relates to a method of dilating an opening in a bodily tissue structure such as an anulus of a human disc. The method A includes providing a surgical device including an outer tube and an inner rod. The outer tube co-axially receives the inner rod and forms a radially expandable head at a distal portion thereof. Further, the inner rod is axially movable relative to the outer shaft and includes a bearing surface for selectively expanding the head between a contracted position and an expanded position. The inner rod is maneuvered relative to the outer tube to orientate the head in the contracted position. The head is then inserted within the opening. Finally, the inner rod is maneuvered relative to the outer tube to orientate the head in the expanded position, thereby dilating the opening.

BRIEF DESCRIPTION OF THE DRAWINGS

FIG. 2A is a side view of an outer tube portion of the dilator of FIG. 1;

FIG. 2B is a cross-sectional view of the outer tube of FIG. 2A along the line 2B—2B;

FIG. 6A is a cross-sectional view of the dilator of FIG. 5 upon final assembly in an undeflected position;

FIG. 6B is a cross-sectional view of a portion of the dilator of FIG. 6A in a deflected position;

DETAILED DESCRIPTION OF THE PREFERRED EMBODIMENTS

Figure 1:
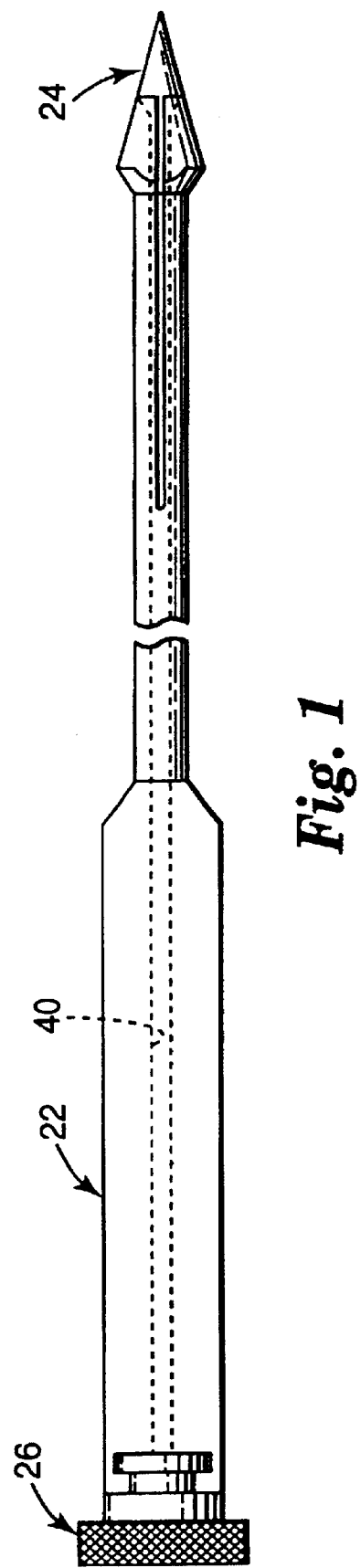
FIG. 1 is a side view of an adjustable surgical dilator in accordance with the present invention.

One preferred embodiment of an adjustable surgical dilator 20 is shown in FIG. 1. The adjustable surgical dilator 20 is comprised of an outer tube 22, an inner rod 24 and a control cap 26. As described in greater detail below, the inner rod 24 is co-axially disposed within the outer tube 22. The control cap 26 retains the inner rod 24 in this position such that the inner rod 24 is axially movable relative to the outer shaft 22.

The outer tube 22 is shown in greater detail in FIG. 2A. In one preferred embodiment, the outer tube 22 includes a handle 30 and a shank 32. The handle 30 defines a proximal section 34, whereas the shank 32 defines a distal section 36. An intermediate section 38 is defined at an intersection of the handle 30 and the shank 32. Finally, a central lumen 40 extends from the proximal section 34 to the distal section 36.

The handle 30 is preferably formed from a rigid, surgically-safe material such as hardened stainless steel. In one preferred embodiment, the handle 30 is configured to provide an elongated, flat surface (shown in FIG. 2A), for facilitating proper handling and indicating to a surgeon (not shown) an orientation of the handle 30 and the shank 32. The proximal section 34 preferably forms a retention body 42 configured to selectively retain the control cap 26 (FIG. 1). Thus, in one preferred. embodiment, the retention body 42 includes an opening 44 defined by opposing fingers 46 and a shoulder 48. The opposing fingers 46 are configured to retain a portion of the control cap 26 within the opening 44 and provide a proximal bearing surface. Conversely, the shoulder 48 provides a distal bearing surface as described in greater detail below. Alternatively, the retention body 42 may assume a wide variety of other forms as will be apparent to one of ordinary skill in the art, and may include additional components, such as springs, bolts, etc.

The shank 32 is similarly formed from a rigid, surgically-safe material such as hardened stainless steel. Alternatively, other materials such as aluminum, Nitinol® composites, etc., can also be employed. The shank 32, and in particular the distal section 36 includes a first arm 60 and a second arm 62 separated by an axial slot 64. The first and second arms 60, 62 combine to define a head 66 terminating in a distal end 68. More particularly, and as shown in FIG. 2, the first arm 60 defines an outer surface 70 and an inner surface 72 defining a portion of the axial slot 64. Similarly, the second arm 62 defines an outer surface 74 and an inner surface 76 defining a portion of the axial slot 64. Notably, while FIG. 2A depicts two of the arms 60, 62, additional arms may further be employed.

The outer surfaces 70, 74 of the arms 60, 62 combine to define the head 66. In one preferred embodiment, the head 66 includes a circumferential stop 78. Further, the head 66 tapers from the circumferential stop 78 to the distal end 68. This tapered configuration facilitates insertion of the head 66 into a small opening (not shown). Finally, in one preferred embodiment, the head 66 further tapers proximally from the circumferential stop 78. As described in greater detail below, a proximal taper of head 66 reduces an overall thickness of the first arm 60 and the second arm 62, thereby enhancing deflectablility of the first arm 60 and the second arm 62.

As shown best in FIG. 2B, the head 66 is radially expandable (as indicated by arrows in FIG. 2B), having a variable, outer cross-sectional dimension. In the preferred embodiment depicted in FIG. 2B, the head 66 has a variable, outer cross-sectional width. Alternatively, the first and second arms 60, 62 can be configured and orientated to provide a variable, outer cross-sectional height, length, diameter, etc. Even further, and as made more clear below, the head 66 may be defined by one or more additional arms (i.e., in addition to the arms 60, 62) such that the head 66 is radially expandable in multiple directions or dimensions.

Returning to FIG. 2A, the axial slot 64 extends from the distal end 68 to a closed end 80. In other words, the first and second arms 60, 62 extend from the closed end 80 to the distal end 68 such that the first and second arms 60, 62 are radially deflectable relative to one another, deflecting or pivoting at the closed end 80. Radial deflection of the first and second arms 60, 62 corresponds with a radial increase in a dimension of the axial slot 64 as well as an increase in an outer dimension of head 66. For example, as shown in FIG. 2B, the slot 64 is preferably configured to increase in width (as shown in FIG. 2B). Alternatively, or in addition, the slot 64 may increase in height, length, diameter, etc. To enhance the ease with which the first and second arms 60, 62 deflect relative to one another, the axial slot 64 (and thus the closed end 80) preferably extends well beyond the head 66 as depicted in FIG. 2A. Thus, a length of the slot 64 (or location of the closed end 80) defines an overall spring force for expansion of the head 66. That is to say, the force required to radially expand the head 66 corresponds with a length of the slot 64. For example, in one preferred embodiment, the head 66 has a length in the range of approximately 5–20 mm, whereas the axial slot 64 has a length of approximately 40–100 mm.

In one preferred embodiment, the handle 30 and the shank 32 are manufactured as separate components. With this configuration, the shank 32 is attached to the handle 30 at an intersection 82. For example, the shank 32 is frictionally received within an opening (not shown) formed in the handle 30. Alternatively, a wide variety of other joining techniques may be employed, including welds, threads, adhesives, etc. Even further, the handle 30 and the shank 32 may be integrally formed.

Figure 3:
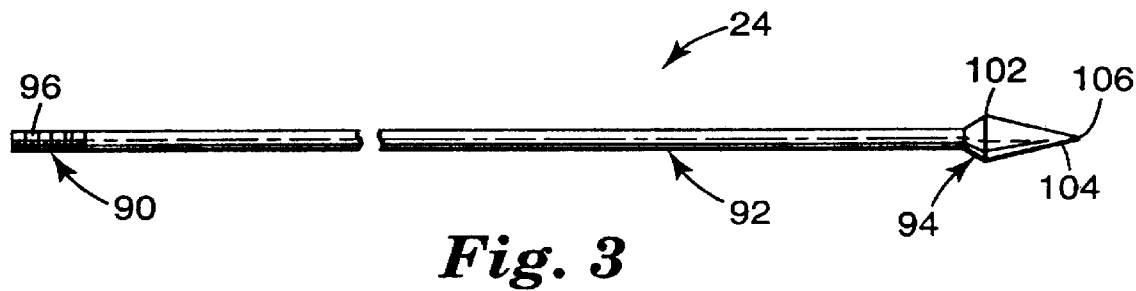
FIG. 3 is a side view of an inner rod portion of the dilator of FIG. 1.

The inner rod 24 is shown in greater detail in FIG. 3. The inner rod 24 includes a proximal portion 90, an intermediate portion 92 and a distal portion 94. The inner rod 24 is preferably integrally formed from a rigid, surgically safe material such as hardened stainless steel. Alternatively, other rigid materials such as aluminum, titanium, Nitinol ®, polymer composites, etc., may also be useful.

The proximal portion 90 is configured for selective attachment to the control cap 26 (FIG. 1). Thus, in one preferred embodiment, the proximal portion 90 forms threads 96. Alternatively, other attachment configurations may be provided.

The intermediate portion 92 extends from the proximal portion 90 and is sized to be axially received within the central lumen 40 (FIG. 1) of the outer tube 22 (FIG. 1). Thus, the intermediate portion 92 has a diameter slightly less than that of the central lumen 40. Further, in one preferred embodiment, the intermediate portion 92 has a length approximating a length of the outer tube 22.

The distal portion 94 extends from the intermediate portion 92 and preferably includes a bearing surface 102 and a tip 104. As shown in FIG. 3, the bearing surface 102 is preferably frusto-conical, tapering proximally. The bearing surface 102 is configured to selectively engage the first and second arms 60, 62 (FIG. 2A), and thus has an outer dimension, preferably a diameter, slightly greater than a corresponding dimension of the axial slot 64 (FIG. 2B). As described below, a taper of the bearing surface 102 can be increased or decreased from that shown to effectuate a different deflection rate of the first and second arms 60, 62. The tip 104 is conical in form, tapering distally from the bearing surface 102. In this regard, the tip 104 is configured to partially dilate a small opening, preferably terminating in a point 106.

Figure 4:
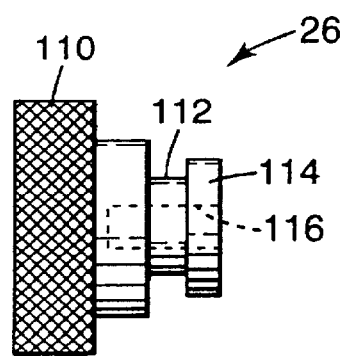
FIG. 4 is a side view of a screw cap of the dilator of FIG. 1.

The control cap 26 is shown in greater detail in FIG. 4. The control cap 26 includes a top 110, a neck 112 and a flange 114. Further, the control cap 26 forms an internal thread 116 extending centrally through the flange 114 and the neck 112. The control cap 26 is preferably formed from a rigid, surgically-safe material such as hardened stainless steel. Alternatively, other materials such as aluminum, Nitinol®, composites or combinations thereof, etc., can also be used. In one preferred embodiment, an outer surface of the top 110 is knurled to facilitate grasping by a user. The neck 112 and the flange 114 extend from the top 110 and are preferably configured to be captured by the retention body 42 (FIG. 2A) of the outer tube 22 (FIG. 2A) as described below.

Figure 5:
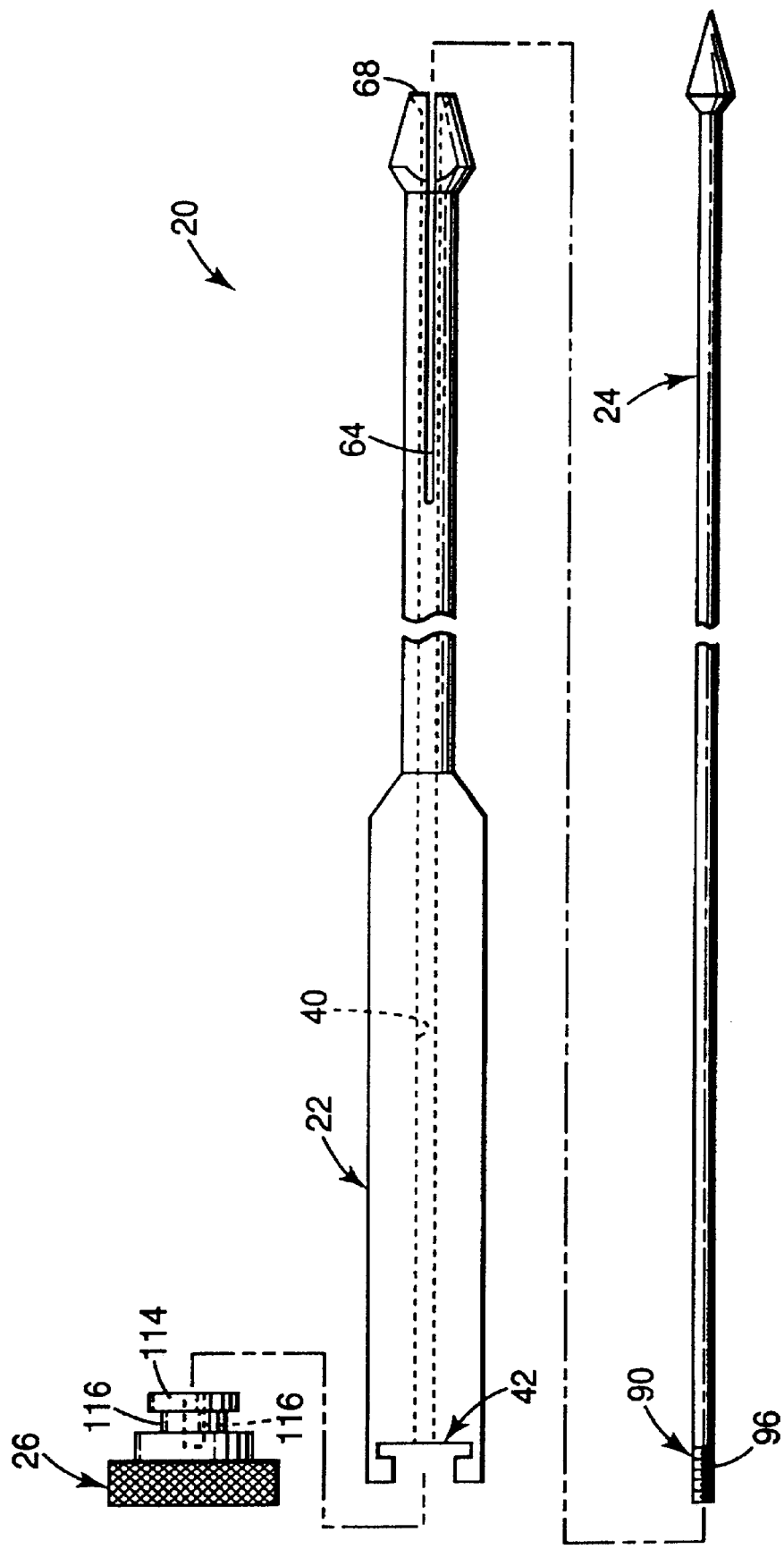
FIG. 5 is an exploded view of the dilator of FIG. 1.

Assembly of the adjustable anulus dilator 20 is shown in FIG. 5. The control cap 26 is positioned relative to the outer tube 22 such that the flange 114 and the neck 112 are captured by the retention body 42. The proximal portion 90 of the inner rod 24 is axially maneuvered into the axial slot 64 of the outer tube 22 at the distal end 68 thereof. The inner rod 24 is then slid proximally within the central lumen 40 until the threads 96 engage the internal threads 116 of the control cap 26. Once threadably engaged, rotation of the control cap 26 causes the inner rod 24 to move axially within the central lumen 40 of the outer tube 22.

A relationship of the outer tube 22, the inner rod 24 and the control cap 26 upon final assembly is best shown in FIGS. 6A and 6B. As a point of reference, the adjustable anulus dilator 20 is depicted in FIG. 6 in a first, pre-dilation position. In this first position, the inner rod 24 is axially positioned such that the tip 104 is substantially contiguous with the distal end 68 of the outer tube 22. That is to say, a distal taper of the head 66 (as defined by the outer surfaces 70, 74 of the first and second arms 60, 62) is substantially contiguous with a taper of the tip 104. Further, the bearing surface 102 is substantially disengaged from the inner surfaces 72, 76 of the first and second arms 60, 62, respectively. Thus, in the first, pre-dilation position, the bearing surface 102 does not impart a radial deflection between the first and second arms 60, 62 such that the first and second arms 60, 62, and thus the head 66, are in a relaxed or undeflected position.

Rotation of the control cap 26 causes a proximal, axial movement (retraction) of the inner rod 24 relative to the outer tube 22 via a threading engagement between the threads 96 (FIG. 5) and the internal threaded portion 116. Retraction of the inner rod 24 causes the bearing surface 102 to engage the inner surfaces 72, 76 of the first and second arms 60, 62 due to the bearing surface 102 having a dimension greater than a corresponding dimension of the axial slot 64. For example, the bearing surface 102 preferably has a width that is greater than a width of the axial slot 64. By engaging the inner surfaces 72, 76, the bearing surface 102 causes the first and second arms 60, 62 to radially deflect at the closed end 80. Deflection of the first and second arms 60, 62 corresponds with an expansion of the head 66 as shown in FIG. 6B, which represents a second, dilation position of the adjustable anulus dilator 20. Obviously, further retraction of the inner rod 24 results in an increased deflection of the first and second arms 60, 62, and thus expansion of the head 66. As should be evident from a comparison of FIGS. 6A and 6B, a taper of the bearing surface 102 dictates a rate at which the head 66 expands. For example, the bearing surface 102 may be formed to have a more gradual taper than that shown in FIG. 6A (i.e., the bearing surface 102 is more elongated). During initial retraction of the inner rod 24, and thus initial engagement between the bearing surface 102 and the inner surfaces 72, 76 of the first and second arms 60, 62, radial expansion of the head 66 occurs more slowly than would otherwise be achieved with similar initial retraction of the configuration of FIG. 6A. Conversely, a more drastic taper of the bearing surface 102 will effectuate a more rapid initial expansion. As such, taper of the bearing surface 102 can be varied to accommodate the needs of a particular application.

Figure 6C:
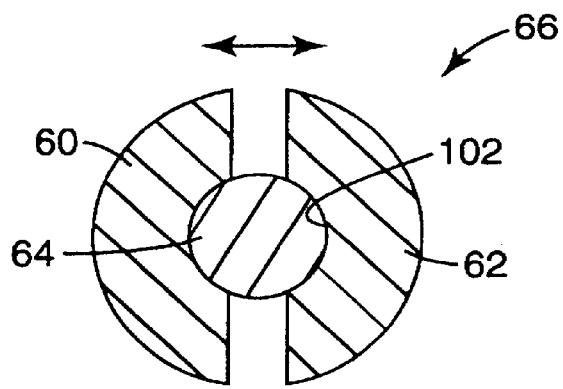
FIG. 6C is a cross-sectional view of the dilator of FIG. 6B along the line 6C—6C.
Figure 6D:
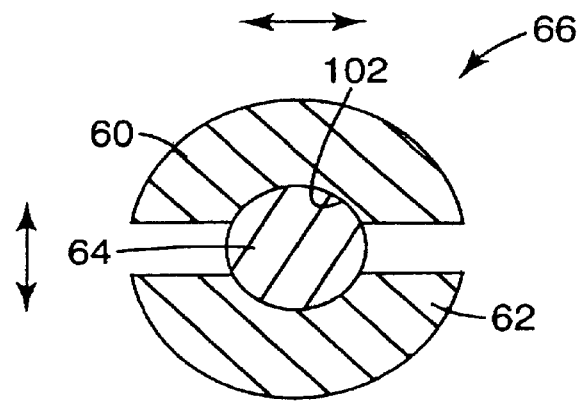
FIGS. 6D and 6E are cross-sectional views of alternative dilators in accordance with the present invention.
Figure 6E:
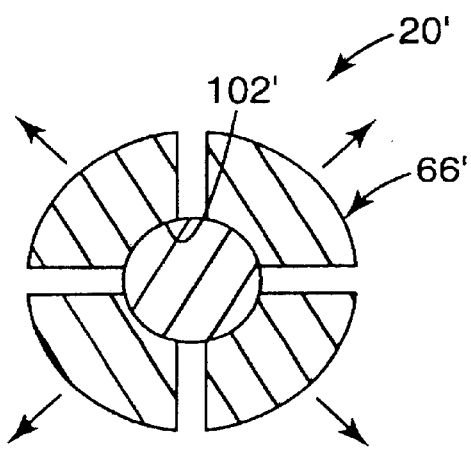
Figure 7:
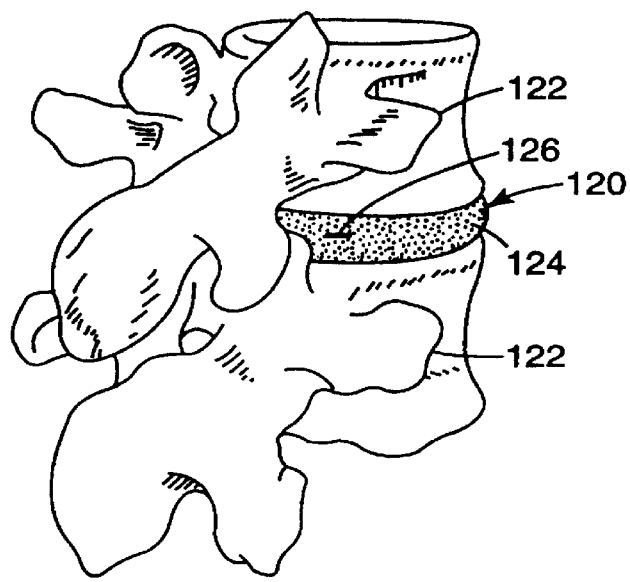
FIG. 7 is a posterior view of a portion of a human spine.

As shown in FIG. 6C, axial movement of the bearing surface 102 causes the head 66 to preferably expand in cross-sectional width (as indicated by arrows in FIG. 6C). Alternatively, a cross-sectional height of the head 66 may be affected as shown, for example, in FIG. 6D. Even farther, FIG. 6E depicts an alternative dilator 20' having a head 66' defined by four arms. Engagement with a bearing surface 102' causes the head 66' to expand in multiple cross-sectional dimensions (indicated by arrows in FIG. 6E).

FIGS. 7–10 depict use of the adjustable anulus dilator 20 with a damaged disc space 120. The disc space 120 separates adjacent vertebrae 122 and includes an anulus 124 surrounding a nucleus region or cavity 125 (shown best in FIG. 8). Access to the nucleus region 125, for example to implant a prosthetic nucleus, can be gained by dilating a small opening or incision 126 in the anulus 124. The opening 126 may be "preformed," appearing as a tear or other defect in the anulus 124. Alternatively, the opening 126 can be created by a surgeon in the form of a small incision.

Figure 8:
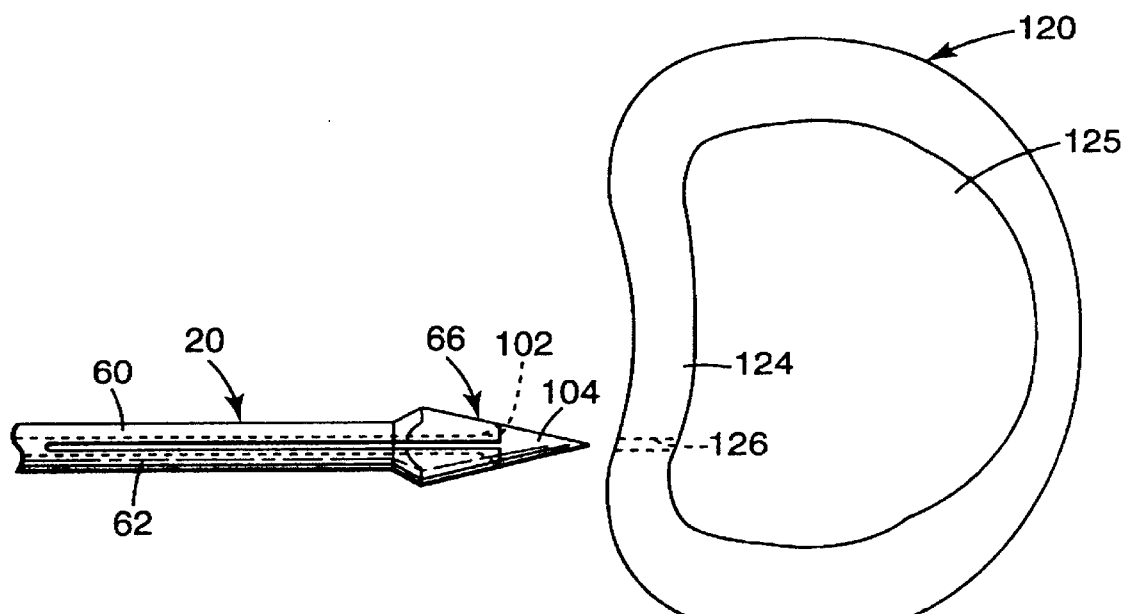
FIGS. 8–10 depict use of dilator in accordance with the present invention in dilating an opening associated with a anulus of a human disc.

The adjustable anulus dilator 20 is then directed toward the opening 126 as shown in FIG. 8. Notably, prior to contact with the anulus 124, the adjustable anulus dilator 20 is positioned in the first, pre-dilation position whereby the tip 104 extends distal the head 66 and the bearing surface 102 does not engage the first and second arms 60, 62. Thus, the head 66 assumes an undeflected or relaxed position. As the adjustable anulus dilator 20 is further directed toward the anulus 124, the tip 104 engages and passes into the opening 126. Due to the tapered shape of the tip 104, the tip 104 will easily pass into the opening 126.

Figure 9:
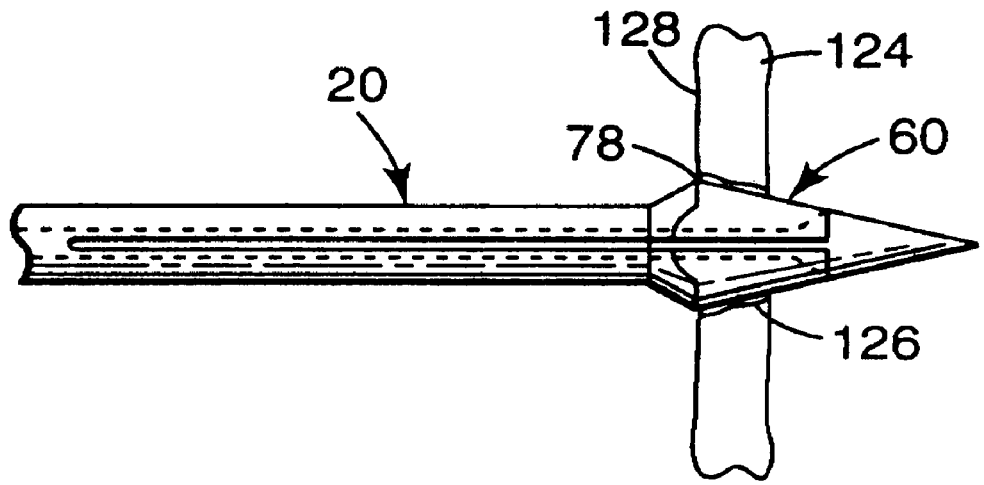

Distal movement of the adjustable surgical dilator 20 continues until the circumferential stop 78 contacts an outer surface 128 of the anulus 124 as shown in FIG. 9. Contact between the circumferential stop 78 and the anulus 124 provides the surgeon with a perceptible impediment to further movement, thereby indicating proper positioning of the head 66 relative to the anulus 124. As should be evident by comparison of FIG. 8 with FIG. 9, the tapered shape of the head 66 causes a slight dilation in the opening 126.

Figure 10:
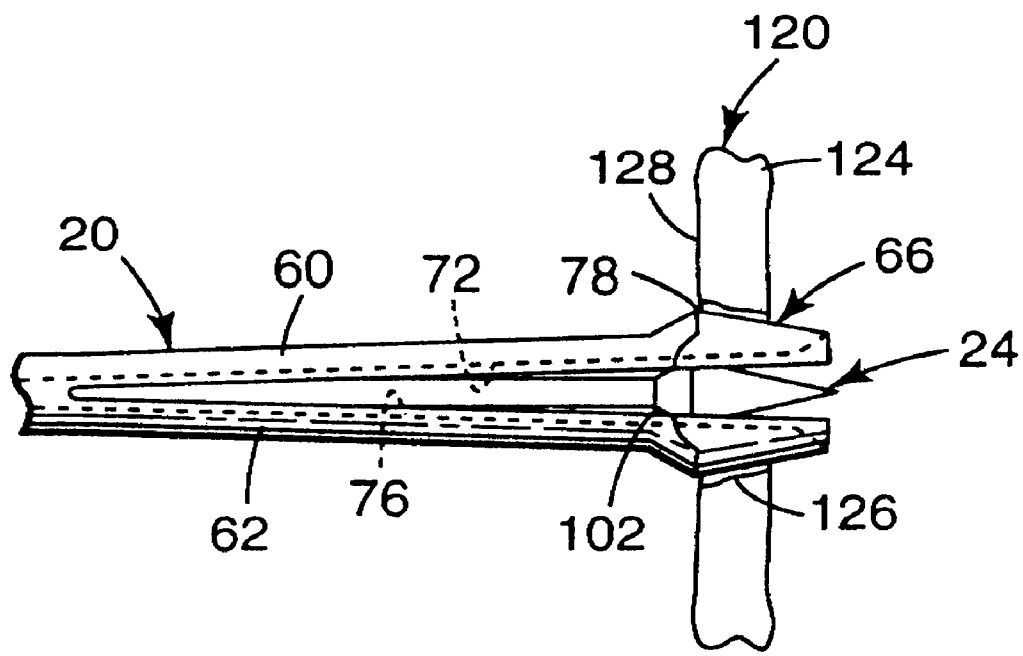

Once properly positioned, the head 66 is expanded to further dilate the opening 126, as shown in FIG. 10. More particularly, and as previously described, the inner rod 24 is retracted such that the bearing surface 102 engages the inner surfaces 72, 76 of the first and second arms 60, 62. Further proximal movement of the inner rod 24 causes the first and second arms 60, 62 to deflect such that the head 66 expands radially. Notably, and with reference to FIG. 6A, the surgeon can control the rate at which dilation occurs by rotating the control cap 26 slowly or rapidly. Notably, by observing the number of revolutions of the control cap 26, the surgeon can accurately estimate actual dilation of the opening 126 in that rotation of the cap 26 corresponds with an expansion position of the head 66 via engagement of the bearing surface 102 with the first and second arms 60, 62.

Once the opening 126 has been sufficiently dilated, the inner rod 24 is advanced distally relative to the outer tube 22. With the distal movement of the inner rod 24, the spring force associated with the first and second arms 60, 62 causes the first and second arms 60, 62 to contract (or relax) toward the undetected position (FIG. 1). Movement of the inner rod 24 continues until the first and second arms 60, 62, and therefore the head 66, is fully contracted, or when the surgeon "feels" that the head 66 has disengaged the anulus 124. The adjustable anulus dilator 20 is then removed from the disc space 120. The resulting dilated opening 126 is now sufficiently large to facilitate insertion of a prosthetic disc nucleus (not shown) or similar device.

Figure 11:
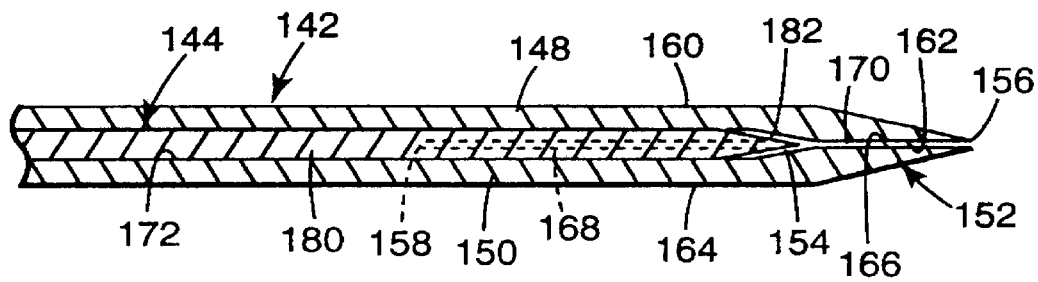
FIG. 11 is a side, cross-sectional view of a portion of an alternative adjustable surgical dilator in accordance with the present invention.

While the adjustable surgical dilator 20 has been described as including the inner rod 24 configured for proximal movement to effectuate expansion of the head 66, other configurations are acceptable. For example, an alternative adjustable surgical dilator 140 is shown in FIG. 11. For ease of illustration, only a distal portion of the adjustable dilator 140 is shown in FIG. 11. The adjustable surgical dilator 140 includes an outer tube 142, an inner rod 144 and a control device (not shown). The outer tube 142 includes a distal section 146 including a first arm 148 and a second arm 150 that combine to define a head 152. The first and second arms 148, 150 are separated by an axial slot 154 that extends proximally from a distal end 156 to a closed end 158. With this configuration in mind, the first arm 148 defines an outer surface 160 and an inner surface 162; similarly, the second arm 150 defines an outer surface 164 and an inner surface 166. As with previous embodiments, the first arm 148 and the second arm 150 are deflectable relative to one another at the closed end 158, whereby the closed end 158 defines a spring force of the first and second arms 148, 150. With this configuration, the head 152 has a variable outer cross-sectional dimension, for example a variable cross-sectional width. Finally, the axial slot 154 is defined by a first section 168 and a second section 170. The first section 168 is connected to a central lumen 172 formed by the outer tube 142 and tapers to the second section 170. The second section 170 extends from the first section 168 to the distal end 156.

The inner rod 144 includes a distal portion 180 forming a bearing surface 182. As shown in FIG. 11, the bearing surface 182 preferably is conical in shape, tapering distally. Notably, the bearing surface 182 has a maximum outer dimension less than a corresponding dimension of the first section 168 of the axial slot 154, and larger than a corresponding dimension of the second section 170 of the axial slot 154. For example, in one preferred embodiment, the bearing surface 182, the first section 168 of the axial slot 154 and the second section 170 of the axial slot 154 are circular in cross-section. With this configuration, the bearing surface 182 has a maximum outer diameter less than a diameter of the first section 168 and larger than a diameter of the second section 170. Finally, as with the previous embodiment, the inner rod 144 is sized to be co-axially disposed within the central lumen 172 of the outer tube 142.

During use, the adjustable dilator 140 provides for selected expansion of the head 152 via axial movement of the inner rod 144 relative to the outer tube 142. As a point of reference, the adjustable dilator 140 is shown in FIG. 11 in a contracted or relaxed position, whereby the bearing surface 182 of the inner rod 144 has not engaged the inner surfaces 162, 166 of the first and second arms 148, 150, respectively. Following positioning of the head 152 within a tissue opening (such as the opening in an anulus as previously described), the inner rod 144 is maneuvered distally. With distal movement of the inner rod 144, the bearing surface 182 engages the inner surfaces 162, 166 of the first and second arms 148, 150, respectively. Engagement of the bearing surface 182 causes the first and second arms 148, 150 to deflect at the closed end 158, such that the head 152 expands radially outwardly, for example in width, height or diameter. In other words, the axial slot 154, and in particular the second section 170, expands outwardly. Distal movement of the inner rod 144 relative to the outer tube 142 continues until the head 152 has expanded to a desired, dilated position. Subsequent proximal movement of the inner rod 144 allows the first and second arms 148, 150 to contract or relax, such that the head 152 disengages the tissue being dilated, thereby allowing for removal of the adjustable surgical dilator 140.

Figure 12:
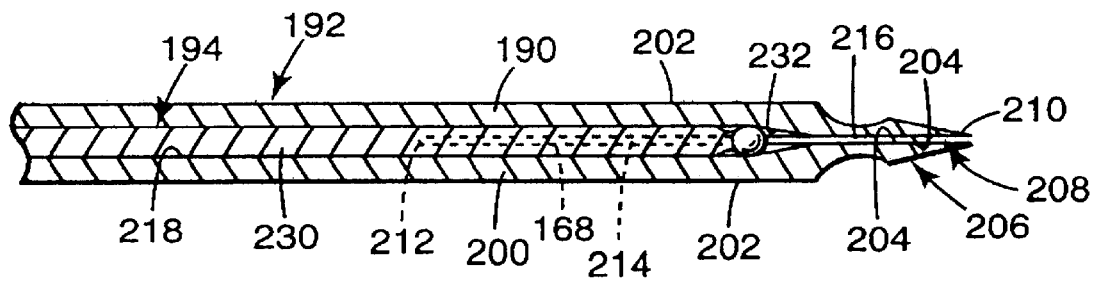
FIG. 12 is a side, cross-sectional view of a portion of an alternative adjustable surgical dilator in accordance with the present invention.

Yet another alternative embodiment of an adjustable surgical dilator 190 is shown in FIG. 12. As with previous embodiments, the adjustable surgical dilator 190 includes an outer tube 192, an inner rod 194 and a control device (not shown). The outer tube 192 co-axially receives the inner rod 194 and includes a distal section 196 having a first arm 198 and a second arm 200. The first and second arms 198, 200 each include an outer surface 202 and an inner surface 204, respectively. The outer surfaces 202 combine to define a head 206. Unlike previous embodiments, the head 206 as defined by the outer surfaces 202 is not linear. That is to say, the head 206 can assume a wide variety of shapes selected for engaging a particular tissue structure. Regardless, the head 206 again provides a variable outer cross-sectional dimension (e.g., width, height and/or diameter) due to a deflectability of the arms 198, 200. The inner surfaces 204 are separated by an axial slot 208 extending proximally from a distal end 210 to a closed end 212. In this regard, the axial slot 208 defines a first section 214 and a second section 216, with the first section 214 connected to a central lumen 218 and tapering to the second section 216.

The inner rod 194 is sized to be co-axially received within the central lumen 218 and includes a distal portion 230 forming a bearing surface 232. The bearing surface 232 is configured to selectively engage the inner surfaces 204 of the first and second arms 198, 200, respectively. Unlike previous embodiments, the bearing surface 232 is substantially spherical in shape. Thus, as should be evident to one of ordinary skill in the art, the bearing surface 232 (or the bearing surfaces 102, 182) can assume a wide variety of shapes, including conical, frusto-conical, spherical, rectangular, square, etc.

During use, distal movement of the inner rod 194 relative to the outer tube 192 causes the bearing surface 232 to engage the inner surfaces 204 of the first and second arms 198, 200. Upon engagement, the first and second arms 198, 200 deflect radially outwardly, pivoting at the closed end 212. Deflection of the first and second arms 198, 200 correspond with an expansion of the second section 216 of the axial slot 208, and thus of the head 206. Thus, following placement of the head 206 within a tissue opening, distal movement of the inner rod 194 expands the head 206, thereby dilating the opening in question.

The adjustable surgical dilator of the present invention provides a marked improvement over previous dilation instruments and techniques. The adjustable surgical dilator of the present invention eliminates the need for three or more separate tools, and instead provides a singular tool configured to provide for sufficient dilation. Further, the adjustable surgical dilator affords a surgeon the ability to control the rate at which dilation occurs, as well as a final dilation size.

Although the present invention has been described with reference to preferred embodiments, workers skilled in the art will recognize that changes may be made in form and detail without departing from the spirit and scope of the present invention. For example, use of the adjustable surgical dilator has been described with specific reference to spinal disc anulus applications. However, the adjustable surgical dilator can be used to dilate an opening formed in any bodily tissue structure, such as an organ, joint, etc. Depending upon the particular application, sizing of the particular components comprising the adjustable surgical dilator will vary accordingly. Additionally, while the dilator has been described as preferably including a control cap, other configurations for maintaining the inner rod relative to the outer tube can be employed. For example, the inner rod may be frictionally maintained within the outer tube, with a portion of the inner rod extending proximally therefrom. With this design, a surgeon directly grasps and manipulates the inner rod. Thus, the control cap, and apparent alterations thereof, is not a necessary element. Even further, alternative axial movement control assemblies can be incorporated. For example, axial movement of the inner rod relative to the outer tube can be controlled by a lever mechanism, a gear assembly, etc.

What is claimed is:

1. An adjustable surgical dilator for dilating an opening formed in a bodily tissue structure, the dilator comprising:
   an outer tube including:
      a proximal section,
      a distal section extending from the proximal section and terminating in a distal end, the distal section including first and second arms each defining an inner surface and an outer surface, wherein the arms combine to define a head tapering to the distal end, the head being configured to releasably contact bodily tissue and having a variable cross-sectional outer dimension defined by the outer surfaces of the arms,
      a central lumen extending from the proximal section to the distal section; and
   an inner rod co-axially disposed within the central lumen, the inner rod including:
      a proximal portion,
      a distal portion extending from the proximal portion, the distal portion forming a bearing surface for selectively engaging the inner surfaces of the first and second arms, respectively, to control the variable cross-sectional outer dimension of the head;
   wherein the inner rod is axially moveable relative to the outer tube for providing selective positioning of the bearing surface relative to the arms, the bearing surface being positioned to initially engage the inner surfaces proximate the distal end, and further wherein the outer tube and the inner rod are adapted such that movement of the bearing surface in a first axial direction causes continuous engagement with the inner surfaces and a corresponding continuous increase in the cross-sectional outer dimension of the head.

2. The dilator of claim 1, further including a tapered tip formed by at least one of the outer rod and the inner tube for initially engaging bodily tissue at a pre-formed opening.

3. The dilator of claim 2, wherein the tapered tip is formed at the distal portion of the inner rod.

4. The dilator of claim 3, wherein the tapered tip is distal the bearing surface.

5. The dilator of claim 4, wherein the tapered tip is adjacent the bearing surface such that the bearing surface is configured to taper proximally and the tapered tip tapers distally.

6. The dilator of claim 5, wherein the inner rod is configured to be movable between a first, insertion position in which the tapered tip extends distal the distal end of the outer tube and a second, expansion position in which at least a portion of the tapered tip is proximal the distal end.

7. The dilator of claim 1, wherein proximal movement of the bearing surface causes an increase in the variable cross-sectional outer dimension of the head.

8. The dilator of claim 1, wherein distal movement of the bearing surface causes an increase in the variable cross-sectional outer dimension of the head.

9. The dilator of claim 1, wherein the bearing surface is tapered.

10. The dilator of claim 1, wherein the bearing surface is substantially spherical.

11. The dilator of claim 1, wherein the inner surfaces are substantially parallel.

12. The dilator of claim 1, further comprising:
a control cap connected to the proximal portion of the inner rod for movably retaining the inner rod relative to the outer tube.

13. The dilator of claim 1, wherein the variable cross-sectional outer dimension is a width of the head.

14. The dilator of claim 1, wherein the head includes a non-linear surface.

15. The dilator of claim 1, wherein a distal segment of the head forms a stop for resisting axial movement of the surgical dilator upon contact with bodily tissue.

16. The surgical dilator of claim 1, wherein the bearing surface is positioned to initially engage the inner surfaces at the distal end.

17. An adjustable surgical dilator for dilating an opening formed in a bodily tissue structure, the dilator comprising:
an outer tube including:
a proximal section,
a distal section extending from the proximal section and terminating in a distal end, the distal section including:
a head tapering distally to the distal end, the head being configured to releasably contact bodily tissue,
an axial slot extending from the distal end to a point proximal the head,
wherein an outer cross-sectional dimension of the head varies with radial expansion of the axial slot,
a central lumen extending from the proximal section to the axial slot; and
an inner rod co-axially disposed within the central lumen, the inner rod including:
a proximal portion,
a distal portion extending from the proximal portion, the distal portion forming a bearing surface configured to selectively engage the distal section of the outer tube to control the radial expansion of the slot;
wherein the inner rod is axially movable relative to the outer tube for providing selective positioning of the bearing surface relative to the distal section of the outer tube, the bearing surface being positioned to initially engage the distal section proximate the distal end, and further wherein the outer tube and the inner rod are adapted such that movement of the bearing surface in a first axial direction causes continuous engagement with the distal section and a corresponding continuous radial expansion of the axial slot.

18. The dilator of claim 17, wherein the bearing surface forces the axial slot to a first radial expansion in a first engaged position and to a second radial expansion in a second engaged position, the first radial expansion being less than the second radial expansion.

19. The dilator of claim 17, wherein the distal portion of the inner rod further includes a tapered tip formed distal the bearing surface for initially engaging bodily tissue at a preformed opening.

20. The dilator of claim 19, wherein the inner rod is movable relative to the outer tube such that in a first, insertion position, the tapered tip is distal the distal end and in a second, expansion position, at least a portion of the tapered tip is proximal the distal end.

21. The dilator of claim 20, wherein the tapered tip is configured to be substantially contiguous with the head in the first position.

22. The dilator of claim 17, wherein the bearing surface is tapered.

23. The dilator of claim 17, wherein the bearing surface is curved.

24. The dilator of claim 17, further comprising:
a control cap connected to the proximal portion of the inner rod for movably retaining the inner rod relative to the outer tube.

25. The dilator of claim 17, wherein the outer cross-sectional dimension is a width of the head.

26. The dilator of claim 17, wherein the head includes a non-linear surface.

27. The dilator of claim 17, wherein a distal segment of the head forms a stop for resisting axial movement of the surgical dilator upon contact with bodily tissue.

28. The surgical dilator of claim 17, wherein the bearing surface is positioned to initially engage the distal section at the distal end.

29. A method of dilating an opening in an anulus of a human disc, the method comprising:
providing an adjustable surgical dilator including an outer tube and an inner rod, the outer tube co-axially receiving the inner rod and forming an expandable head at a distal portion thereof, wherein the inner rod is axially movable relative to the outer shaft and includes a bearing surface for selectively expanding the head between a contracted position and an expanded position, the outer tube and the inner rod being adapted such that movement of the inner rod relative to the outer tube in a first axial direction causes a corresponding, continuously increasing expansion of the head;
maneuvering the inner rod relative to the outer tube such that the head is in the contracted position;
forming an opening in an anulus of a human disc;
inserting the head within the opening; and
maneuvering the inner rod relative to the outer tube such that the head is in the expanded position to dilate the opening.

30. The method of claim 29, wherein the dilator further includes a control cap threadably receiving a portion of the inner rod, and further wherein maneuvering the inner rod relative to the outer tube such that the head is in the expanded position includes:
rotating the control cap to axially move the bearing surface into engagement with the outer tube.

31. The method of claim 29, wherein maneuvering the inner rod relative to the outer tube such that the head is in the expanded position includes:
retracting the inner rod proximally relative to the outer tube such that the bearing surface engages the outer tube.

32. The method of claim 29, wherein maneuvering the inner rod relative to the outer tube such that the head is in the expanded position includes:
extending the inner rod distally relative to the outer tube such that the bearing surface engages the outer tube.

33. The method of claim 29, wherein the head terminates at a distal end, and further wherein maneuvering the inner rod relative to the outer tube such that the head is in the expanded position includes:

causing the bearing surface to initially contact the head proximate the distal end.

\* \* \* \* \*